United States Patent

Krämer et al.

Patent Number: 4,918,093
Date of Patent: Apr. 17, 1990

[54] HYDROXYETHYL-AZOLYL OXIMES AND ETHERS THEREOF USEFUL AS FUNGICIDES

[75] Inventors: Wolfgang Krämer; Karl H. Büchel, both of Burscheid; Graham Holmwood, Wuppertal; Stefan Dutzmann, Duesseldorf; Paul Reinecke, Leverkusen, all of Fed. Rep. of Germany

[73] Assignee: Bayer Aktiengesellschaft, Leverkusen, Fed. Rep. of Germany

[21] Appl. No.: 218,718

[22] Filed: Jul. 13, 1988

[30] Foreign Application Priority Data

Jul. 31, 1987 [DE] Fed. Rep. of Germany ....... 3725396

[51] Int. Cl.$^4$ .................. A01N 43/653; C07C 249/08
[52] U.S. Cl. ................................... 514/383; 548/267.4
[58] Field of Search .......................... 548/262; 514/383

[56] References Cited

U.S. PATENT DOCUMENTS 4,622,335 11/1986 Krämer et al. ...................... 514/383
4,645,767 2/1987 Holmwood et al. ................. 514/383

FOREIGN PATENT DOCUMENTS 0141204 5/1985 European Pat. Off. .
0176998 4/1986 European Pat. Off. .
3307218 9/1984 Fed. Rep. of Germany .
3407005 4/1985 Fed. Rep. of Germany .
3436452 4/1986 Fed. Rep. of Germany .

*Primary Examiner*—Richard L. Raymond
*Assistant Examiner*—Peter G. O'Sullivan
*Attorney, Agent, or Firm*—Sprung, Horn, Kramer & Woods

[57] ABSTRACT

Hydroxyethyl-azolyl oxime ethers of the formula

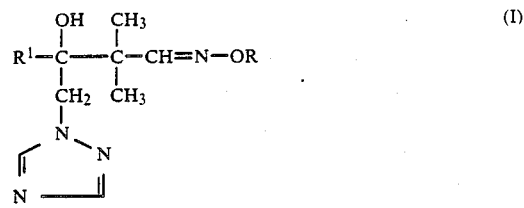

in which
R represents hydrogen, alkyl with 1 to 6 carbon atoms or alkenyl with 2 to 6 carbon atoms and
$R^1$ represents the radicals of the formula

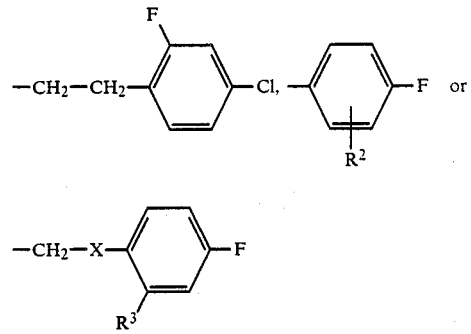

wherein
$R^2$ represents hydrogen, fluorine or chlorine,
$R^3$ represents hydrogen, fluorine or chlorine and
X represents oxygen, sulphur or a $CH_2$ group,
and acid addition salts and metal salt complexes thereof. Such hydroxyethyl-azolyl oxime ethers are useful as fungicides.

7 Claims, No Drawings

HYDROXYETHYL-AZOLYL OXIMES AND ETHERS THEREOF USEFUL AS FUNGICIDES

The present invention relates to new hydroxyethyl-azolyl oxime ethers, several processes for their preparation and their use as fungicides.

It has already been disclosed that certain hydroethyl-azolyl derivatives have fungicidal properties (compare EP-OS (European Published Specification) 0 141 204). Thus, for example, 2-(4-chlorophenyl)-3-methyl-3-propoximinomethyl-1-(1,2,4-tri-azol-1-yl)-butan-2-ol, 2-(4-chlorophenyl)-3-methyl-3-cyclohexyl-methoximinomethyl-1-(1,2,4-triazol-1-yl)-butan-2-ol and 2-(4-chlorophenyl)-3-methyl-3-n-butoximinomethyl-1-(1,2,4-triazol-1-yl)-butan-2-ol can be used for combating phytopathogenic fungi. The activity of these compounds is good, but they leave something to be desired in some cases when used in low application amounts.

New hydroxyethyl-azolyl oxime ethers of the formula

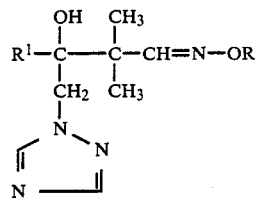

(I)

in which
R represents hydrogen, alkyl with 1 to 6 carbon atoms or alkenyl with 2 to 6 carbon atoms and
$R^1$ represents the radicals of the formula

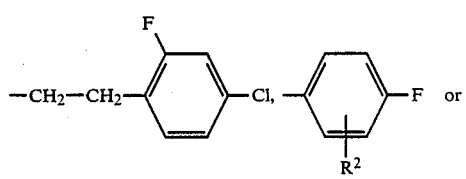

wherein
$R^2$ represents hydrogen, fluorine or chlorine,
$R^3$ represents hydrogen, fluorine or chlorine and
X represents oxygen, sulfur or a $CH_2$ group,
and acid addition salts and metal salt complexes thereof have now been found.

It has furthermore been found that hydroxyethylazolyl oxime ethers of the formula (I) and acid addition salts and metal salt complexes thereof are obtained by a process in which
(a) hydroxyethyl-azolyl acetals of the formula

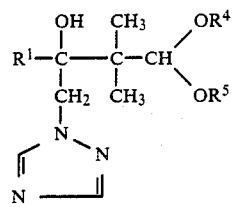

(IIa)

in which
$R^1$ has the abovementioned meaning,
$R^4$ represents alkyl with 1 to 4 carbon atoms and
$R^5$ represents alkyl with 1 to 4 carbon atoms, or
$R^4$ and $R^5$ together represents a $-CH_2-CH_2-$ group,
or hydroxyethyl-azolyl-aldehydes of the formula

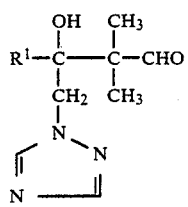

(IIb)

in which $R^1$ has the abovementioned meaning, are reacted with hydroxylamine compounds of the formula $$H_2N-OR \qquad (III)$$

in which R has the abovementioned meaning, or with hydrochlorides of hydroxylamine compounds of the formula (III), in the presence of a diluent and if appropriate in the presence of a catalyst, or
(b) hydroxyethyl-azolyl oxime derivatives of the formula

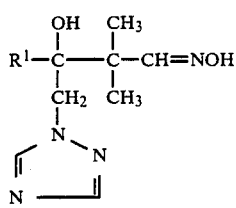

(Ia)

in which $R^1$ has the abovementioned meaning, are reacted with halogen compounds of the formula $$Hal-R^6 \qquad (IV)$$

in which
Hal represents chlorine, bromine or iodine and
$R^6$ represents alkyl with 1 to 6 carbon atoms or alkenyl with 2 to 6 carbon atoms,
in the presence of a diluent and if appropriate in the presence of an acid-binding agent, or
(c) oxiranes of the formula

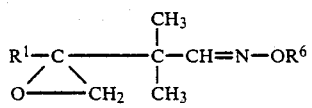

(V)

in which $R^6$ and $R^1$ have the abovementioned meanings, are reacted with 1,2,4-triazole of the formula

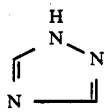

(VI)

in the presence of a diluent and, if appropriate, in the presence of an acid-binding agent, and, if appropriate, an acid or a metal salt is then added onto the compounds of the formula (I) thus obtained.

Finally, it has been found that the new hydroxyethyl-azolyl oxime ethers of the formula (I) and acid addition salts and metal salt complexes thereof have powerful fungicidal properties.

Surprisingly, the substances according to the invention exhibit a better fungicidal activity than 2-(4-chlorophenyl)-3-methyl-3-propoximinomethyl-1-(1,2,4-triazol-1-yl)-butan-2-ol, 2-(4-chlorophenyl)-3-methyl-3-cyclohexylmethoximinomethyl-1-(1,2,4-triazol-1-yl)-butan-2-ol and 2-(4-chlorophenyl)-3-methyl-3-n-butoximinomethyl-1-(1,2,4-triazol-1-yl)-butan-2-ol, which are structurally the most similar already known active compounds of the same type of action.

Formula (I) provides a general definition of the hydroxyethyl-azolyl oxime ethers according to the invention. Preferred compounds are those in which R represents hydrogen, methyl, ethyl, n-propyl, ispropyl, n-butyl, isobutyl, sec.-butyl, tert.-butyl or allyl and $R^1$ represents the radicals of the formula

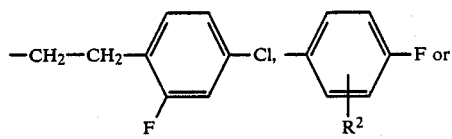

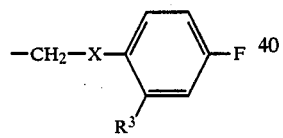

wherein $R^2$ represents hydrogen, fluorine or chlorine, $R^3$ represents hydrogen, fluorine or chlorine and X represents oxygen, sulphur or a $CH_2$ group.

Addition products of acids and those hydroxy-ethylazolyl oxime ethers of the formula (I) in which R and $R^1$ have the meanings which have already been mentioned as preferred for these radicals are also preferred compounds according to the invention.

The acids which can be added on include, preferably, hydrogen halide acids, such as, for example, hydrochloric acid and hydrobromic acid, in particular hydrochloric acid, and furthermore phosphoric acid, nitric acid, sulphuric acid, mono- and bifunctional carboxylic acids and hydroxycarboxylic acids, such as, for example, acetic acid, maleic acid, succinic acid, fumaric acid, tartaric acid, citric acid, salicyclic acid, sorbic acid and lactic acid, and sulphonic acids, such as, for example, p-toluenesulfonic acid, 1,5-naphthalenedisulphonic acid or camphorsulphonic acid, and saccharine.

Addition products of salts of metals of main group II to IV and sub-group I and II and IV to VIII of the periodic table of the elements and those hydroxy-ethylazolyl oxime ethers of the formula (I) in which R and $R^1$ have the meanings which have already been mentioned as preferred for these radicals, are also preferred compounds according to the invention.

Salts of copper, zinc, manganese, magnesium, tin, iron and nickel are particularly preferred here. Possible anions of these salts are those which are derived from acids which lead to physiologically tolerated addition products.

Particularly preferred acids of this type are, in this connection, the hydrogen halide acids, such as, for example, hydrochloric acid and hydrobromic acid, and furthermore phosphoric acid, nitric acid and sulphuric acid.

If 2-(2-dioxolanyl)-3-(4-fluorophenyl)-2-methyl-4-(1,2,4-triazol-1-yl)-butan-3-ol and O-methylhydroxylamine hydrochloride are used as starting substances and concentrated hydrochloric acid is used as the catalyst, the course of process (a) according to the invention can be illustrated by the following equation:

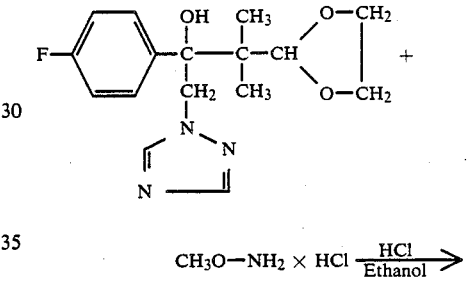

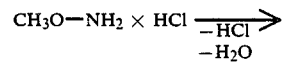

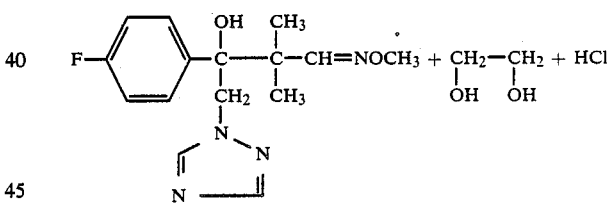

If 3-(2,4-difluoro-phenyl)-2,2-dimethyl-3-hydroxy-4-(1,2,4-triazol-1-yl)-butan-1-al and O-methylhydroxylamine hydrochloride are used as starting substances, the course of process (a) according to the invention can be illustrated by the following equation:

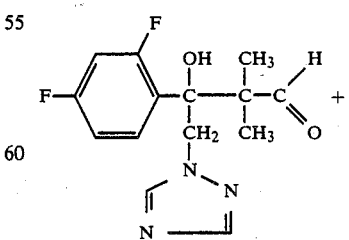

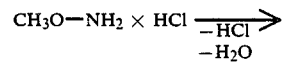

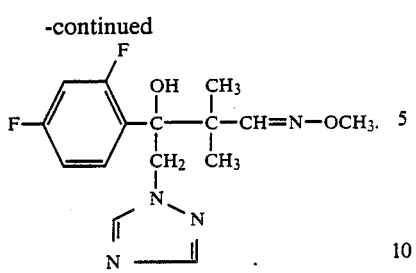

If 3-(4-fluoro-phenyl)-2-hydroximinomethyl-2-methyl-4-(1,2,4-triazol-1-yl)-butan-3-ol and allyl chloride are used as starting substances, the course of process (b) according to the invention can be illustrated by the following equation:

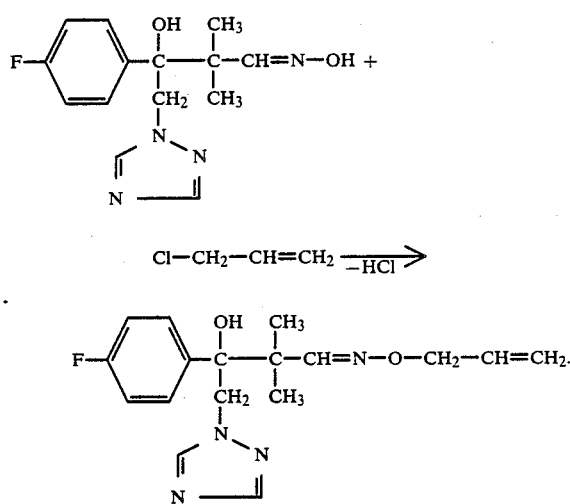

If 2-(4-fluoro-phenyl)-2-(2-methoximinomethyl-2-propyl)-oxirane and 1,2,4-triazole are used as starting substances, the course of process (c) according to the invention can be illustrated by the following equation:

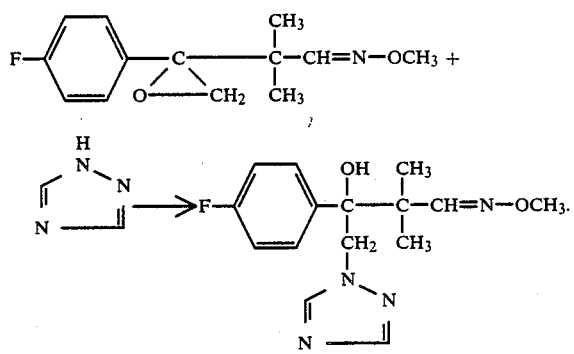

Formula (IIa) provides a general definition of the hydroxyethyl-azolyl acetals required as starting substances in carrying out process (a) according to the invention. In this formula, $R^1$ preferably has those meanings which have already been mentioned as preferred for $R^1$ in connection with the description of the substances according to the invention. $R^4$ and $R^5$ preferably represent methyl or ethyl or together represent a —$CH_2$—$CH_2$— group.

The hydroxyethyl-azolyl acetals of the formula (IIa) can be prepared by a process in which oxiranes of the formula

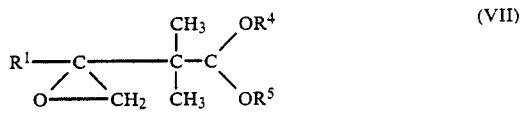

in which $R^1$, $R^4$ and $R^5$ have the abovementioned meanings, are reacted with 1,2,4-triazole of the formula

in the presence of an inert organic diluent, such as, for example, an alcohol, and if appropriate in the presence of an acid-binding agent, such as a sodium alcoholate or potassium hydroxide, at temperatures between 60° C. and 150° C. (compare the preparation examples).

The oxiranes of the formula (VI) can be prepared by a process in which ketones of the formula

in which $R^1$, $R^4$ and $R^5$ have the abovementioned meanings, either (α) are reacted with dimethyloxosulphonium methylide of the formula

in a manner which is known per se in the presence of a diluent, such as, for example, dimethylsulphoxide, at temperatures between 20° C. and 80° C. (in this context, compare the information in *J. Am. Chem. Soc.*, 87, 1363–1364 (1965)), or (β) are reacted with trimethylsulphonium methyl-sulphate of the formula $$[(CH_3)_3S^{\oplus}]\ CH_3SO_4^{\ominus} \quad (X)$$

in a manner which is known per se in the presence of an inert organic solvent, such as, for example, acetonitrile, and in the presence of a base, such as, for example, sodium ethylate, at temperatures between 0° C. and 60° C., preferably at room temperature (compare also the information in *Heterocycles*, 8, 397 (1977)).

If appropriate, the oxiranes of the formula (VII) thus obtained can be further reacted directly without being isolated.

The ketones of the formula (VIII) can be prepared by a process in which 1-(N-morpholino)-isobutene of the formula

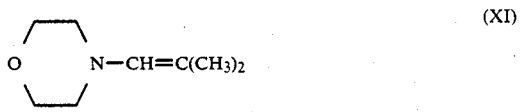

is reacted with chlorides of the formula $$R^1—CO—Cl \quad (XII)$$

in which $R^1$ has the abovementioned meaning, in the presence of a solvent, such as, for example, diethyl ether, at temperatures between 20° C. and 120° C. and the keto derivatives thus obtained, of the formula

(XIII)

in which $R^1$ has the abovementioned meaning, are converted into the corresponding acetals with the aid of alcohols, such as methanols, ethanol or ethylene glycol, in the presence of an inert organic diluent, such as toluene, and in the presence of a strong acid, such as p-toluenesulphonic acid, as the catalyst, at temperatures between 80° C. and 110° C.

Formula (IIb) provides a general definition of the hydroxyethyl-azolyl-aldehydes furthermore required as starting substances in process (a) according to the invention. In this formula, $R^1$ preferably has those meanings which have already been mentioned as preferred for this radical in connection with the description of the substances of the formula (I) according to the invention.

The hydroxyethyl-azolyl-aldehydes of the formula (IIb) can be prepared by a process in which hydroxyethylazolyl acetals of the formula

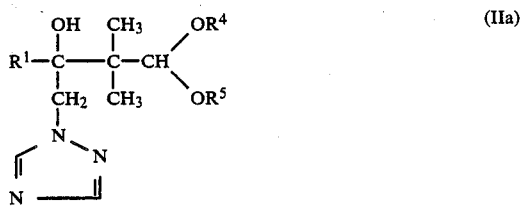
(IIa)

in which $R^1$, $R^4$ and $R^5$ have the abovementioned meanings, are reacted in the presence of a mixture of water and a water-miscible inert organic solvent, such as methanol or ethanol, and in the presence of an inorganic or organic acid, such as hydrochloric acid, sulphuric acid, p-toluensulphonic acid or acetic acid, at temperatures between 30° C. and 120° C., preferably at the boiling point of the solvent used.

Formula (III) provides a general definition of the hydroxylamine compounds required as reaction components in carrying out process (a) according to the invention. In this formula, R preferably represents those radicals which have already been mentioned as preferred for this radical in connection with the description of the substances of the formula (I) according to the invention.

The hydroxylamine compounds of the formula (III) and their hydrochlorides are generally known compounds of organic chemistry.

Diluents which can be used in carrying out process (a) according to the invention are all the solvents customary for such reactions. Preferred possible solvents are alcohols and water and mixtures thereof.

Possible catalysts in carrying out process (a) according to the invention are all the reaction accelerators customary for such reactions. Reaction accelerators which can preferably be used are strong inorganic and organic acids, such as hydrochloric acid and p-toluenesulphonic acid.

The reaction temperatures can be varied within a substantial range in carrying out process (a) according to the invention. The reaction is in general carried out at temperatures between 20° C. and 120° C., preferably between 50° C. and 100° C.

In carrying out process (a) according to the invention, 1 to 1.5 mol of hydroxylamine compound of the formula (III) and if appropriate a catalytic amount of reaction accelerator are preferably employed per mol of a compound of the formula (IIa) or (IIb). The compounds of the formula (I) are worked up and isolated by customary methods. In a preferred embodiment of process (a) according to the invention, the hydroxylamine compounds of the formula (III) are used in the form of their hydrochlorides.

The hydroxyethyl-azolyl oxime ethers of the formula (Ia) to be used as starting substances for carrying out process (b) according to the invention are compounds according to the invention.

Formula (IV) provides a general definition of the halogen compounds also to be used as starting substances for carrying out process (b) according to the invention. In this formula, Hal preferably represents methyl, ethyl, n-propyl, iso-propyl, n-butyl, iso-butyl, sec.-butyl, tert.-butyl or allyl.

The halogen compounds of the formula (IV) are generally known compounds of organic chemistry.

Possible diluents in carrying out process (b) according to the invention are inert organic solvents. Solvents which can preferably be used as ethers, such as tetrahydrofuran and dioxane; aromatic hydrocarbons, such as toluene and benzene; in individual cases also chlorinated hydrocarbons, such as chloroform, methylene chloride or carbon tetrachloride; and hexamethylphosphoric acid triamide, acid amides, such as dimethylformamide, and sulphoxides, such as dimethylsulphoxide.

Possible acid-binding agents in carrying out process (b) according to the invention are strong bases. Bases which can preferably be used are alkali metal amides, hydrides, hydroxides and carbonates, such as, for example, sodium amide, carbonate, hydroxide or hydride and potassium amide, carbonate, hydroxide or hydride, and quaternary ammonium hydroxides and phosphonium hydroxides, such as, for example, tetramethylammonium hydroxide, benzyltrimethyl-ammonium hydroxide or dibenzyl-dimethyl-ammonium hydroxide and tetraphenylphosphonium hydroxide or methyltriphenylphosphonium hydroxide.

The reaction temperatures can be varied within a substantial range in process (b). The reaction is in general carried out between 20° C. and 150° C., preferably at room temperature. In individual cases, it is advantageous to carry out the reaction at the boiling point of the solvent, for example between 60° C. and 100° C.

In carrying out process (b) according to the invention, 1 to 3 mol of halogen compound of the formula (IV) are preferably employed per mol of the compounds of the formula (Ia). To isolate the end products, the reaction mixture is freed from the solvent, and water and an organic solvent are added to the residue. The organic phase is separated off, worked up in the customary manner and purified.

In a preferred embodiment of process (b), the reaction according to the invention is carried out in a two-phase system, such as, for example, aqueous sodium hydroxide solution or potassium hydroxide solution/toluene or methylene chloride, with the addition of 0.01 to 1 mol of a phase transfer catalyst, such as, for example, ammonium or phosphonium compounds, whereupon the alcoholates are formed in the organic phase or at the interfaces and are reacted with the halogen compounds present in the organic phase.

Formula (V) provides a general definition of the oxiranes required as starting compounds in carrying out process (c) according to the invention. In this formula, $R^6$ and $R^1$ preferably have those meanings which have already been mentioned as preferred for these radicals in connection with the description of the compounds of the formula (I) according to the invention and the halogen compounds of the formula (IV).

The oxiranes of the formula (V) have not previously been disclosed. They can be prepared by a process in which keto-oxime derivatives of the formula

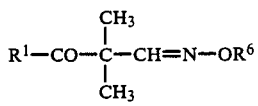  (XIV)

in which $R^1$ and $R^6$ have the abovementioned meanings, either (α) are reacted with dimethyloxosulphonium methylide of the formula

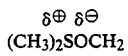  (IX)

in the presence of a diluent, such as dimethylsulphoxide, at temperatures between 20° C. and 80° C., or (β) are reacted with trimethylsulphonium methyl-sulphate of the formula

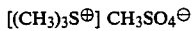  (X)

in the presence of an inert organic solvent, such as acetonitrile, and in the presence of a base, such as sodium methylate, at temperatures between 0° C. and 60° C., preferably at room temperature.

The keto-oxime derivatives of the formula (XIV) can be prepared by a process in which 1-(N-morpholino)isobutene of the formula (XI) is reacted with chlorides of the formula (XII) in the presence of a solvent, such as, for example, diethyl ether, at temperatures between 20° C. and 120° C. and the keto derivatives thus obtained, of the formula (XIII), are derivatized on the aldehyde group in the customary manner by means of hydroxylamine compounds of the formula (III) or hydrochlorides thereof, such as, for example, methoxyhydroxylamine hydrochloride, in the presence of an inert organic solvent, such as, for example, ethanol, and in the presence of sodium acetate at temperatures between 80° C. and 110° C. In some cases, it proves advantageous to introduce the radical $R^1$ or parts thereof only after derivatization of the aldehyde group.

The 1,2,4-triazole of the formula (VI) required as a reaction component for carrying out process (c) according to the invention is known. It can be employed as the free base or in the form of its sodium or potassium salt.

Possible diluents in carrying out process (c) according to the invention are all the organic solvents which are inert under the reaction conditions. Solvents which can preferably be used are alcohols, such as, for example, ethanol, methoxyethanol or propanol; ketones, such as, for example, 2-butanone; nitriles, such as, for example, acetonitrile; esters, such as, for example, ethyl acetate; ethers, such as, for example, dioxane; aromatic hydrocarbons, such as, for example, benzene and toluene; or amides, such as, for example, dimethylformamide.

Possible acid-binding agents in carrying out process (c) according to the invention are all the customary inorganic and organic bases. Bases which can preferably be used are alkali metal carbonates, such as, for example, sodium carbonate and potassium carbonate; alkali metal hydroxides, such as, for example, sodium hydroxide; alkali metal alcoholates; such as, for example, sodium methylate and ethylate and potassium methylate and ethylate; alkali metal hydrides, such as, for example, sodium hydride; and lower tertiary alkylamines, cycloalkylamines and aralkylamines, such as, in particular, triethylamine.

The reaction temperatures can be varied within a substantial range in carrying out process (c) according to the invention. The reaction is in general carried out at temperatures between 0° C. and 200° C., preferably between 60° C. and 150° C.

In carrying out process (c) according to the invention, 1 to 2 mol of 1,2,4-triazole and if appropriate 1 to 2 mol of base are preferably employed per mol of oxirane of the formula (V). The end products are isolated in the generally customary manner.

The hydroxyethyl-azolyl oxime ethers of the formula (I) obtainable by the processes according to the invention can be converted into acid addition salts or metal salt complexes.

Preferred possible acids for the preparation of acid addition salts of the compounds of the formula (I) are those acids which have already been mentioned as preferred acids in connection with the description of the acid addition salts according to the invention.

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and if appropriate purified by washing with an inert organic solvent.

Preferred possible salts of metals for the preparation of metal salt complexes of the compounds of the formula (I) are those salts which have already been mentioned as preferred metal salts in connection with the description of the metal salt complexes according to the invention.

The metal salt complexes of the compounds of the formula (I) can be obtained in a simple manner by customary processes, thus, for example, by dissolving the metal salt in alcohol, for example ethanol, and adding the solution to compounds of the formula (I). The metal salt complexes can be isolated in a known manner, for example by filtration, and if appropriate purified by recrystallization.

The active compounds according to the invention exhibit a powerful microbicidal action and can be used as fungicides.

Fungicides are employed in plant protection for combating Plasmodiophoromycetes, Oomycetes, Chytridiomycetes, Zygomycetes, Ascomycetes, Basidiomycetes and Deuteromycetes.

Some causative organisms of fungal and bacterial diseases which come under the generic names listed above may be mentioned as examples, but not by way of limitation: Xanthomonas species, such as *Xanthomonas oryzae;* Pseudomonas species, such as *Pseudomonas lachrymans;* Erwinia species, such as *Erwinia amylovora;* Pythium species, such as *Pythium ultimum;* Phytophthora species, such as *Phytophthora infestans;* Pseudoperonospora species, such as *Pseudoperonospora humuli* or *Pseudoperonospora cubense;* Plasmopara species, such as *Plasmopara viticola;* Peronospora species, such as *Peronospora pisi* or *P. brassicae;* Erysiphe species, such as *Erysiphe graminis;* Sphaerotheca species, such as *Sphaerotheca fuliginea;* Podosphaera species, such as *Podosphaera leucotricha;* Venturia species, such as *Venturia inaequalis;* Pyrenophora species, such as *Pyrenophora teres* or *P. graminea* (conidia form: Drechslera, syn: Helminthosporium); Cochliobolus species, such as *Cochliobolus sativus* (conidia form: Drechslera, syn: Helminthosporium); Uromyces species, such as *Uromyces appendiculatus;* Puccinia species, such as *Puccinia recondita;* Tilletia species, such as *Tilletia caries;* Ustilago species, such as *Ustilago nuda* or *Ustilago avenae;* Pellicularia species, such as *Pellicularia sasakii;* Pyricularia species, such as *Pyricularia oryzae;* Fusarium species, such as *Fusarium culmorum;* Botrytis species, such as *Botrytis cinerea;* Septoria species, such as *Septoria nodorum;* Leptosphaeria species, such as *Leptosphaeria nodorum;* Cercospora species, such as *Cercospora canescens;* Alternaria species, such as *Alternaria brassicae* and Pseudocercosporella species, such as *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds according to the invention are particularly suitable for combating cereal diseases and rice diseases.

*Pseudocercosporella herpotrichoides* on wheat and barley can thus be combated particularly well.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example, mineral oil fractions, alcohols, such as butanol or glycol as well as their ethers and esters, ketones, such as acetones, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example, aerosol propellants, such as halogenated hydrocarbons as well as butane, propane, nitrogen and carbon dioxide; as solid carriers there are suitable: for example, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example, crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example, non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysation products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oil.

It is possible to use colorants such as inorganic pigments, for example, iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, and in mixtures with fertilizers and other growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seed of the plants can also be treated.

When the substances according to the invention are used, the amount applied can be varied within a substantial range depending on the nature of the application. In the treatment of parts of plants, the active compound concentrations in the use forms are thus in general between 1 and 0.0001% by weight, preferably between 0.5 and 0.001%. In the treatment of seed, amounts of active compound of 0.001 to 50 g per kilogram of seed, preferably 0.01 to 10 g, are generally required. For the treatment of soil, active compound concentrations of 0.00001 to 0.1% by weight, preferably 0.0001 to 0.02% by weight, are required at the place of action.

The preparation and use of the active compounds according to the invention can be seen from the following examples.

PREPARATION EXAMPLES

Example 1

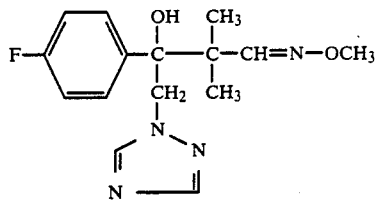

A mixture of 215 g (0.67 mol) of 2-(2-dioxolanyl)-3-(4-fluoro-phenyl)-2-methyl-4-(1,2,4-triazol-1-yl)-butan-3-ol, 75.2 g (0.9 mol) of O-methyl-hydroxylamine hydrochloride, 4 ml of concentrated hydrochloric acid and 800 ml of ethanol is heated under reflux for 5 hours. The solvent is then stripped off under reduced pressure. 1,000 ml of saturated aqueous sodium bicarbonate solution and 1,000 ml of methylene chloride are then added to the residue which remains. The phases are separated, the aqueous phase is extracted twice with 800 ml of methylene chloride each time and the combined organic phases are dried over sodium sulphate and concentrated by stripping off the solvent under reduced pressure. 800 ml of diisopropyl ether are added to the residue and the mixture is filtered with suction. 190 g (93% of theory) of 3-(4-fluoro-phenyl)-2-methoximinomethyl-2-methyl-4-(1,2,4-triazol-1-yl)-butan-3-ol are obtained in this manner in the form of a colourless solid of melting point 98°-101° C.

Preparation of starting substances

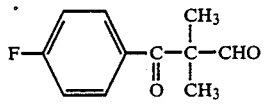

300 g (1.89 mol) of 4-fluoro-benozyl chloride are added dropwise to a solution of 266 g (1.89 mol) of 1-morpholinyl-2-methyl-prop-1-ene in 800 ml of tetrahydrofuran at 5° C. in the course of 3 hours, while stirring and cooling. The reaction mixture is first stirred at room temperature for 15 hours and then heated under reflux for 2 hours and is subsequently cooled to 10° C. The solid which crystallizes out is filtered off with suction, washed twice with 100 ml of tetrahydrofuran each time and then stirred into a mixture of 1,000 ml of water and 1,000 ml of methylene chloride. The phases are separated and the organic phase is concentrated by stripping off the solvent under reduced pressure. 295 g of 2-(4-fluoro-benzoyl)-2-methyl-propionaldehyde remain in the form of a yellow oil.

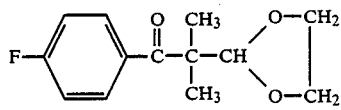

295 g (1.5 mol) of 2-(4-fluoro-benzoyl)-2-methyl-propionaldehyde are added to a solution of 136 g (2.2 mol) of ethylene glycol and 3 g of p-toluenesulphonic acid in 1,500 ml of methylene chloride at room temperature. The reaction mixture is boiled for 24 hours, using a water separator. The organic phase is washed twice with 2,000 ml of water each time and then dried over sodium sulphate and distilled under reduced pressure. 278 g (77% of theory) of (4-fluoro-benzoyl)-(1-dioxolanyl-1-methyl-ethyl)-ketone are obtained in this manner in the form of a colorless liquid of boiling point 100°-102° C./0.3 mbar.

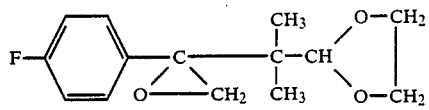

123.1 g (1.1 mol) of potassium tert.-butylate are added to a solution of 242 g (1.1 mol) of trimethyl-sulphonium iodide in 320 ml of dimethylsulphoxide at room temperature. The mixture is stirred at room temperature for 5 hours. Thereafter, 276 g (1.16 mol) of (4-fluoro-phenyl)-(1-dioxolanyl-1-methyl-ethyl)-ketone are added dropwise, with stirring, such that the temperature of the reaction mixture does not rise above 40° C. The mixture is subsequently stirred at 40° C. for a further 16 hours and 1,000 ml of water are then added, while stirring and cooling. The organic phase is separated off, washed twice with 2,000 ml of water each time, dried over sodium sulphate and concentrated by stripping off the solvent under reduced pressure. 280 g of a pale yellow oil which, according to analysis by gas chromatography, consists of 2-(4-fluorophenyl)-2-[1-(2-dioxolanyl)-1-methyl]ethyloxirane to the extent of 84%, are obtained. The yield is accordingly calculated as 80.6% of theory.

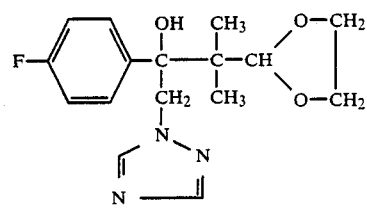

75.9 g (1.1 mol) of 1,2,4-triazole and 7 g of 88% strength aqueous potassium hydroxide solution are added to a solution of 280 g of the crude 2-(4-fluorophenyl)-2-[1-(2-dioxolanyl)-1-methyl]-ethyl-oxirane in 1.1 liters of n-butanol at room temperature. The reaction mixture is heated under reflux for 16 hours, the solvent is then stripped off under reduced pressure, the residue is taken up in 1,000 ml of methylene chloride and the mixture is washed twice with 1,500 ml of water each time.

The organic phase is dried over sodium sulphate and concentrated by stripping off the solvent under reduced pressure. 800 ml of diisopropyl ether are added to the residue which remains. The solid is filtered off with suction and the filtrate is concentrated to a volume of 100 ml by stripping off the solvent under reduced pressure. On cooling to 0° C., a solid crystallizes out and is filtered off with suction. 161 g of 2-(2-dioxolanyl)-3-(4-fluoro-phenyl)-2-methyl-4-(1,2,4-triazol-1-yl)-butan-3-ol are obtained in this manner in the form of a colorless solid of melting point 90° C.

The substances according to the invention shown in the following table are prepared by the method described in Example 1 and in accordance with the information in the description.

TABLE 1

$$R^1-\underset{\underset{\underset{N\diagup\diagdown N}{\underset{\parallel\quad\parallel}{N\longrightarrow}}}{\overset{|}{CH_2}}}{\overset{OH}{\underset{|}{C}}}-\underset{\underset{CH_3}{\overset{|}{C}}}{\overset{CH_3}{\overset{|}{C}}}-CH=N-OR \qquad (I)$$

| Example No. | R¹ | R | Melting point (°C.) |
|---|---|---|---|
| 2 | 4-F-C₆H₄– | –C₃H₇-n | 105 |
| 3 | 4-F-C₆H₄– | –C₄H₉-n | 114 |
| 4 | 4-F-C₆H₄– | –C₂H₅ | 98–100 |
| 5 | 4-F-C₆H₄– | –CH₂–CH=CH₂ | 97–99 |
| 6 | 4-F-C₆H₄– | H | 142–144 |
| 7 | 4-F-C₆H₄–CH₂–CH₂– | H | 101–103 |
| 8 | 4-Cl-2-F-C₆H₃–CH₂–CH₂– | –CH₃ | 83 |
| 9 | 4-Cl-2-F-C₆H₃–CH₂–CH₂– | –C₂H₅ | 55 |
| 10 | 2,4-F₂-C₆H₃–CH₂–CH₂– | –CH₃ | viscous oil |
| 11 | 2,4-F₂-C₆H₃–CH₂–CH₂– | –C₂H₅ | viscous oil |

TABLE 1-continued
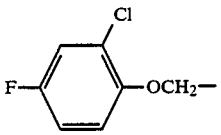  (I)
| Example No. | R¹ | R | Melting point (°C.) |
|---|---|---|---|
| 12 | 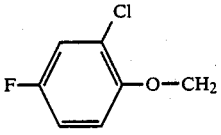 | —CH₃ | 111 |
| 13 | 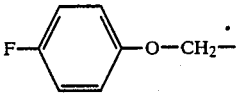 | —C₂H₅ | 116 |
| 14 | 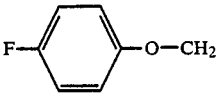 | —CH₃ | 123 |
| 15 | 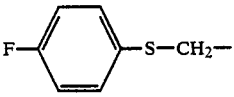 | —C₂H₅ | 121 |
| 16 | 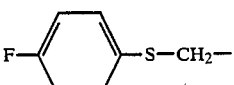 | —CH₃ | viscous oil |
| 17 | 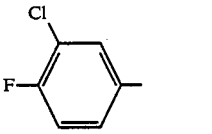 | H | viscous oil |
| 18 | 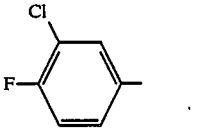 | CH₃ | 90 |
| 19 | 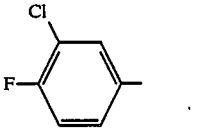 | H | 103–106 |
| 20 | 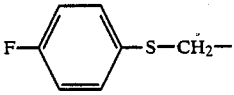 | C₂H₅ | viscous oil |
| 21 | 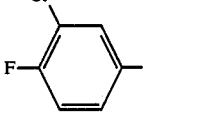 | —C₂H₅ | 133 |

TABLE 1-continued $$\underset{\underset{\underset{N}{\overset{\|}{\underset{\|}{\text{N}}}}{\overset{|}{\text{CH}_2}}}{\overset{\text{OH}}{\underset{|}{\text{R}^1-\text{C}-\text{C}-\text{CH}=\text{N}-\text{OR}}}}\overset{\text{CH}_3}{\underset{\text{CH}_3}{|}} \quad (I)$$

| Example No. | R¹ | R | Melting point (°C.) |
|---|---|---|---|
| 22 | 2-Cl-4-F-phenyl | —CH$_3$ | 131–133 |
| 23 | 2-Cl-4-F-phenyl | —C$_2$H$_5$ | 111–115 |
| 24 | 2-Cl-4-F-phenyl | H | 156–158 |
| 25 | 4-F-phenyl-S-CH$_2$— | —C$_3$H$_7$-n | viscous oil |
| 26 | 3-Cl-4-F-phenyl | —C$_3$H$_7$-n | 128–130 |
| 27 | 2,4-di-F-phenyl | —CH$_2$—CH=CH$_2$ | 112–14 |
| 28 | 2,4-di-F-phenyl | —C$_4$H$_9$-n | 115–17 |
| 29 | 2,4-di-F-phenyl | —CH$_3$ | 127 |
| 30 | 2,4-di-F-phenyl | —C$_2$H$_5$ | 114 |

TABLE 1-continued $$R^1-\underset{\underset{\underset{N\diagdown N}{\underset{\parallel}{\overset{N\diagup}{\underset{\parallel}{\diagdown}}N}}}{\overset{|}{\underset{|}{CH_2}}}}{\overset{OH}{\overset{|}{C}}}-\underset{\underset{CH_3}{\overset{|}{C}}}{\overset{CH_3}{\overset{|}{C}}}-CH=N-OR \quad (I)$$

| Example No. | $R^1$ | R | Melting point (°C.) |
|---|---|---|---|
| 31 | 2,4-difluorophenyl | $-C_3H_7-n$ | 115–117 |

Use Example

The compounds of the formulae shown below were employed as comparison substances in the use example which follows:

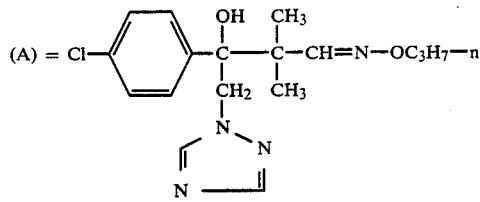

(A) = Cl—C₆H₄—C(OH)(CH₂-triazolyl)—C(CH₃)(CH₃)—CH=N—OC₃H₇—n

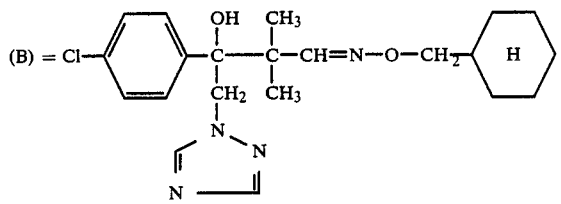

(B) = Cl—C₆H₄—C(OH)(CH₂-triazolyl)—C(CH₃)(CH₃)—CH=N—O—CH₂—cyclohexyl

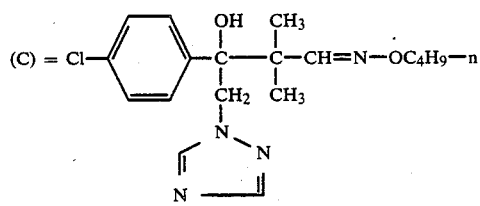

(C) = Cl—C₆H₄—C(OH)(CH₂-triazolyl)—C(CH₃)(CH₃)—CH=N—OC₄H₉—n (known from EP-OS (European Published Specification 0 141 204).

Example A

*Pseudocercosporella herpotrichoides* test (wheat)/protective

Solvent: 100 parts by weight of dimethylformamide
Emulsifier: 0.25 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are inoculated at the stem with spores of *Pseudocercosporella herpotrichoides*.

The plants are placed in a greenhouse at a temperature of about 10° C. and a relative atmospheric humidity of about 80%.

Evaluation is carried out 21 days after the inoculation.

In this test, a better activity than comparison substances (A), (B) and (C) is shown by substances (1), (2), (3), (4) and (5) according to the invention.

It will be appreciated that the instant specification and claims are set forth by way of illustration and not limitation, and that various modifications and changes may be made without departing from the spirit and scope of the present invention.

What is claimed is:

1. A hydroxyethyl-azolyl oxime or ether of the formula

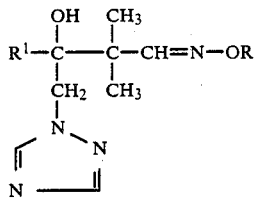

in which
R represents hydrogen, alkyl with 1 to 6 carbon atoms or alkenyl with 2 to 6 carbon atoms and
$R^1$ represents the radicals of the formula

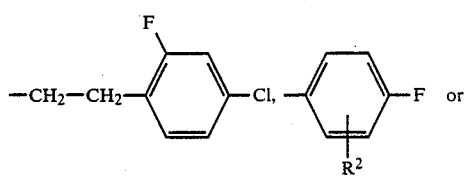

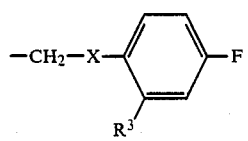

wherein

R² represents hydrogen, fluorine or chlorine,
R³ represents hydrogen, fluorine or chlorine and
X represents oxygen, sulphur or a CH₂ group,
and acid addition salts and metal salt complexes thereof.

2. A hydroxyethyl-azolyl oxime or ether of the formula (I) according to claim 1, in which
R represents hydrogen, methyl, ethyl, n-propyl, isopropyl, n-butyl, isobutyl, sec.-butyl, tert.-butyl or allyl and
R¹ represents the radicals of the formula

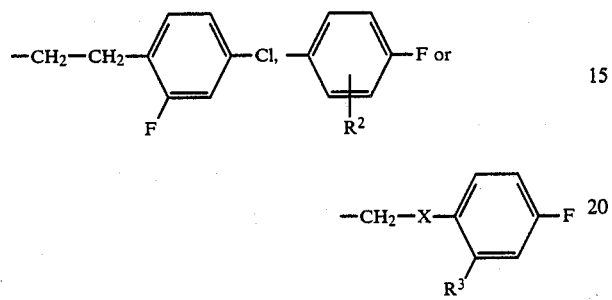

wherein
R² represents hydrogen, fluorine or chlorine,
R³ represents hydrogen, fluorine or chlorine and
X represents oxygen, sulphur or a CH₂ group.

3. A hydroxyethyl-azolyl oxime or ether according to claim 1 of a formula selected from the group consisting of

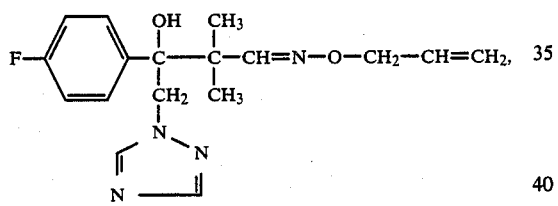

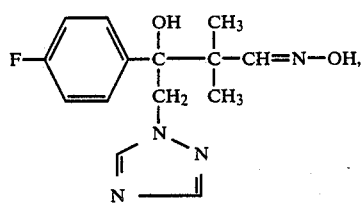

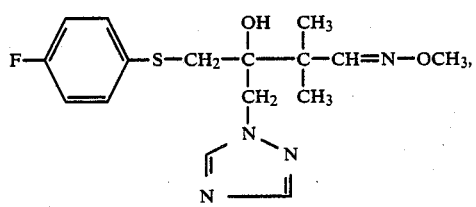

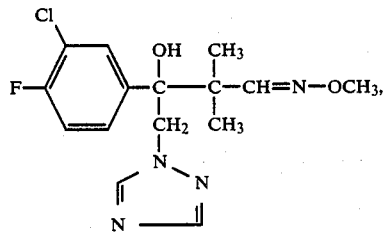

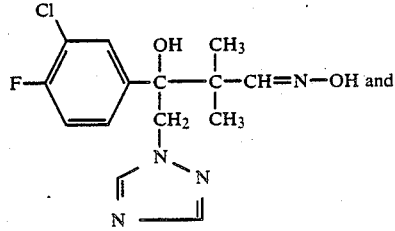

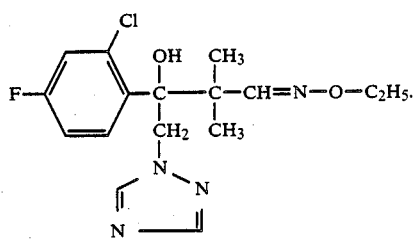

4. A hydroxyethyl-azolyl oxime according to claim 1 of the formula

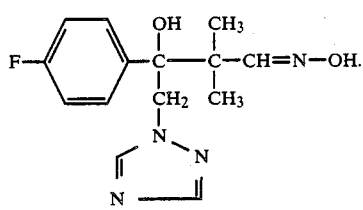

5. A fungicidal composition comprising a fungicidally effective amount of a compound according to claim 1 in admixture with a diluent.

6. A method of combating fungi comprising applying to fungi and/or to an environment thereof a fungicidally effective amount of a hydroxyethyl-azolyl oxime or ether of the formula (I) according to claim 1 or acid addition salts or metal salt complexes thereof.

7. A method according to claim 6, wherein the hydroxyethyl oxime or ether is selected from the group consisting of

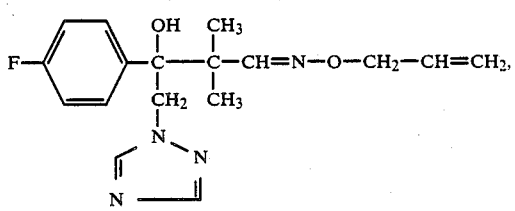

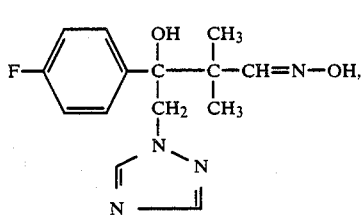

-continued
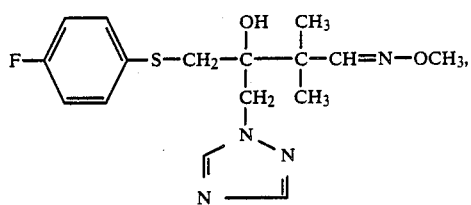
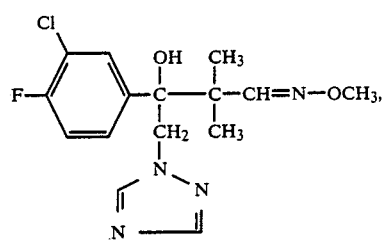
-continued
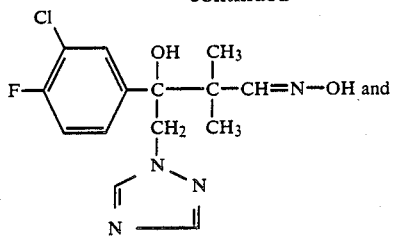
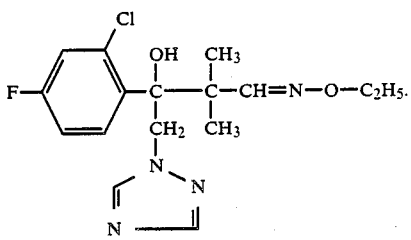
* * * * *